United States Patent [19]

Raftopoulos et al.

[11] 4,337,773
[45] Jul. 6, 1982

[54] METHOD OF AND DEVICE FOR PLACING A BARRIER IN A CAVITY PROVIDED IN A BONE SHAFT

[76] Inventors: Demetrios D. Raftopoulos, 3703 Cherrywood La., Toledo, Ohio 43615; James D. Baril, 465 Canal Ct., Waterville, Ohio 43566

[21] Appl. No.: 198,585

[22] Filed: Oct. 20, 1980

[51] Int. Cl.³ .......................... A61B 17/32; A61F 1/00
[52] U.S. Cl. ............................... 128/305; 128/92 CA; 128/303 R; 128/310; 128/754; 3/1.9; 3/1.913
[58] Field of Search ................................. 3/1.9–1.913; 128/92 C, 92 CA, 303 R, 305, 305.1, 310, 751, 754

[56] References Cited

U.S. PATENT DOCUMENTS

| | | | |
|---|---|---|---|
| 1,123,730 | 1/1915 | Greenfield | 128/310 X |
| 3,850,158 | 11/1974 | Elias et al. | 128/754 |
| 4,245,359 | 1/1981 | Stuhmer | 3/1.91 X |
| 4,266,303 | 5/1981 | Park | 3/1.91 |

FOREIGN PATENT DOCUMENTS

| | | | |
|---|---|---|---|
| 6408 | 1/1980 | European Pat. Off. | 128/92 C |
| 1409054 | 10/1975 | United Kingdom | 3/1.913 |
| 625699 | 9/1978 | U.S.S.R. | 128/305 |

*Primary Examiner*—Ronald L. Frinks

[57] ABSTRACT

An appropriately shaped cavity, formed in a cut femoral bone shaft, is provided with a barrier or plug in its distal portion so that a cement in its liquid state may be injected into the cavity under pressure for causing the cement to flow into the small interstices of the bone forming the cavity.

A preferred method of inserting the plug at a predetermined depth in the cavity generally includes the steps of: (1) forming and retaining the plug in a die; (2) inserting the die containing the plug into the cavity to the predetermined depth; (3) releasing the plug from the die; and (4) injecting the liquid cement under pressure into the plugged cavity.

The device for placing the plug at the predetermined depth in the cavity generally comprises the die, an elongated body member, appropriately shaped so as to be inserted into the cavity and to which the die is detachably connectable, and a pusher member contained within the body member for releasing the plug from the die. Further, the body member is provided with a longitudinally extending scale for determining the depth at which the plug is to be released from the die.

5 Claims, 5 Drawing Figures

METHOD OF AND DEVICE FOR PLACING A BARRIER IN A CAVITY PROVIDED IN A BONE SHAFT

BACKGROUND OF THE INVENTION

1. Field of the Invention

This invention generally relates to a total hip replacement and, more particularly, to a method of and device for providing a barrier at a predetermined depth in a cavity formed in a cut femoral shaft for improving the connection of the femoral prosthesis in the cavity of the femoral shaft.

2. Description of the Prior Art

The concept of implanting a femoral prosthesis in a cut femur by a self-curing cement, of course, is well known in the art. However, only when there is no gap between the prosthesis and the bone can it function effectively in transferring and spreading the weight-bearing forces from the prosthesis to the bony structures of the femur without the loosening or wobbling that ultimately is blamed for the pain and failure encountered in a prosthesis.

In the past, a femoral prosthesis has been attached to a cut femur by self-curing acrylic cements, which have been kneaded to a putty-like consistency and introduced into the cavity prepared in the femur, herein the prosthesis is driven into the cement-filled cavity with a slow steady pressure. This method of cementing a femoral prosthesis to the femur shaft has not been entirely satisfactory in that the intramedullary canal of the femur shaft is relatively hollow, particularly in the more distal portions of the shaft and consequently gaps frequently occur in the cement between the prosthesis and the bony structure of the femur thus not spreading the weight transfer evenly therebetween.

Attempts have been made in the past to employ a cement in the liquid state in the repair of the femur for overcoming the aforementioned problem in this case, a barrier or plug must be created in the intramedullary canal to prevent the liquid cement from being forced distally into the relatively hollow canal. Attempts have been made to provide a barrier at the bottom of the cavity opening into the canal by introducing a small amount of cement at the distal most point that the prosthesis will be inserted into the cavity and allowing it to harden. Although this technique is generally effective, it does have some complications in that, at times, the cement plug, prior to hardening, migrates proximally in the cavity, thus preventing full insertion of the prosthesis. This condition requires removal of the hardened cement plug and not only is the removal thereof a technically difficult task, but the hardening and drying time of the cement is about 15 to 20 minutes which is extremely time consuming in a surgical procedure.

Also attempts have been made in the past to employ plugs made from bone to form a barrier in the intramedullary canal. Although bone plugs work well if properly placed, exact placement thereof in the canal is difficult and inconsistent as they are conventionally inserted in the canal with a hemostat. For example, if a bone plug is not inserted far enough down the canal, the prosthesis will be forced into a malposition resulting in an inadequate placement of the prosthesis.

SUMMARY OF THE INVENTION

Briefly, the present invention contemplates forming and retaining a plug, preferably made from a bone material, in a die which is detachably connectable to an elongated body member which is adapted to be insertable into a preformed cavity provided in a cut femur shaft. The body member is provided with an axially movable pusher member which is adapted to release the bone plug from the die at a predetermined depth in the cavity. Further the body member is provided with a longitudinally extending scale for accurately locating the depth at which the bone plug is positioned in the cavity.

OBJECT AND ADVANTAGES

An object of the invention is to provide a method of and device for accurately positioning a plug at a predetermined depth between a cavity and the intramedullary canal of a femur shaft which is adapted to receiving a femoral prosthesis wherein the prosthesis is secured in the femur by a liquid cement introduced in the cavity under pressure.

Other objects and advantages of the invention will become more apparent during the course of the following description when taken in connection with the accompanying drawings.

BRIEF DESCRIPTION OF THE DRAWINGS

In the drawings wherein like numerals are employed to describe like parts throughout the same.

DESCRIPTION OF THE PREFERRED EMBODIMENT

Figure 1:
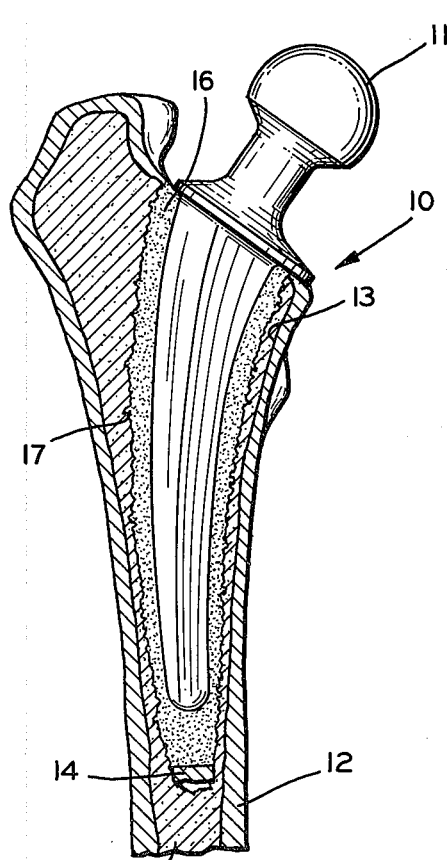
FIG. 1 is a sectional view illustrating a total femoral prosthesis incorporating the invention.

Referring now to the drawings, particularly to FIG. 1, there is illustrated a femoral prosthesis 10 wherein a prosthesis 11 is implanted in a femur shaft 12. As there shown, a cavity 13 formed in a conventional manner in the shaft 12, is provided with a plug 14 located at an exact predetermined depth between the cavity 13 and the somewhat hollow intramedullary canal 15 so that the cavity may be filled with a cement 16 in the liquid state under pressure, for filling the interstices 17 of the bony structure without the cement being forced to distal portions of the canal 15.

Figure 2:
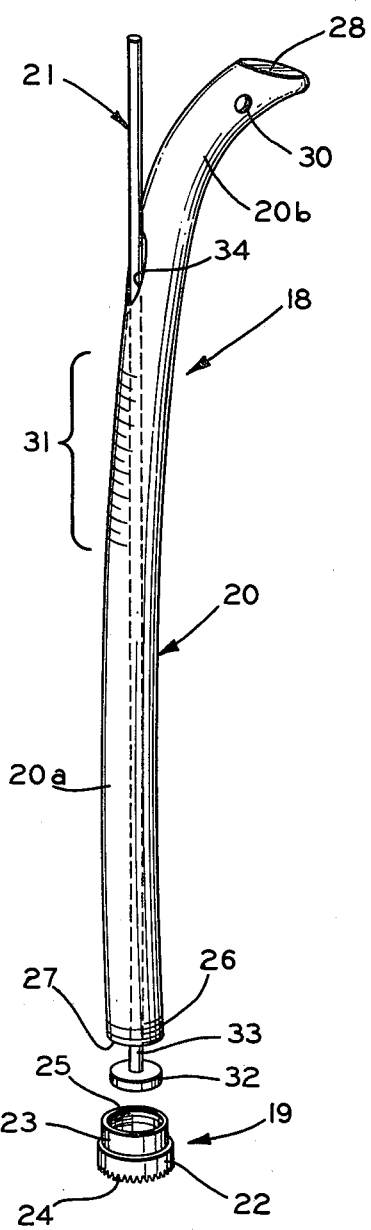
FIG. 2 is an exploded perspective view of the device constructed in accordance with the invention.
Figure 3:
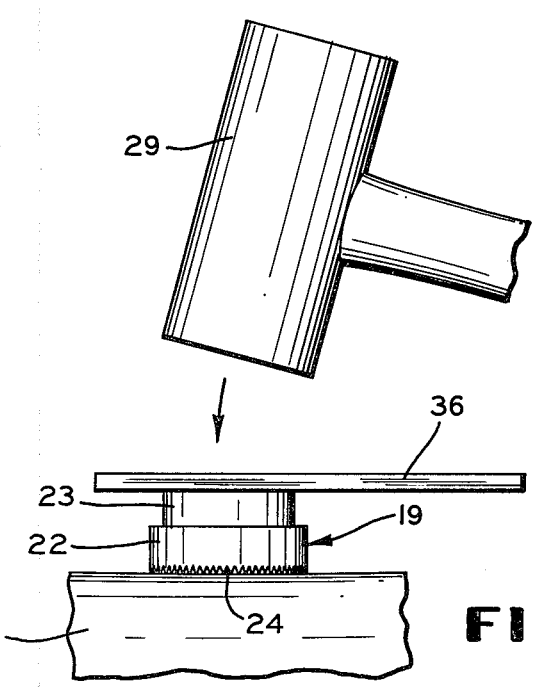
FIG. 3 is an enlarged diagrammatic view of a preferred method of obtaining a plug made from bone.
Figure 4:
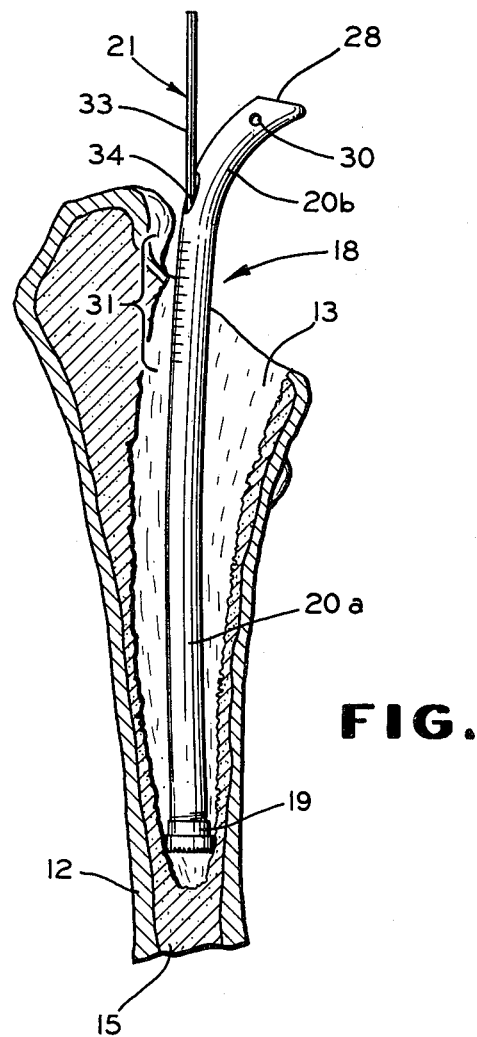
FIG. 4 is a sectional view of the device inserted in a bone cavity.
Figure 5:
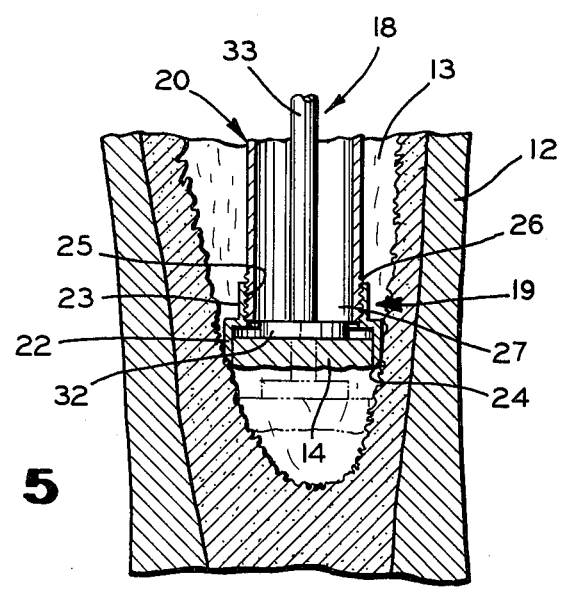
FIG. 5 is an enlarged fragmentary view illustrating the releasing of the bone plug from the device.

To this end, as contemplated by the invention, a device designated in its entirely by the reference numeral 18 and best illustrated in FIG. 2, is provided for cutting the plug 14 and inserting it in the cavity 13 (see FIGS. 3 through 5). Briefly the device 18 comprises a die 19 which is detachable connectably to the end of an elongated hollow body member 20 which is provided with a telescoped, axially movable pusher member 21.

Referring now to FIGS. 2 and 5, the die 19 is formed as a stepped annular member, preferably from a metallic material, having a cutting portion 22 and an attaching portion 23. Serrations or teeth 24 are provided on the bottom periphery of the cutting portion 22 for cutting the plug 14 and the attaching portion 23 is provided with a series of internal threads 25 for threadingly attaching the die 19 to external threads 26 provided on the open end 27 of the body member 20.

In addition to the open threaded end 27, the elongated hollow body member 20 is provided with a longitudinal curved shape which is similar to the longitudinal curved shape of the conventional reamers and rasps (not shown) used in forming the cavity 13 so that the device 18 may be inserted in the cavity in the proper position for depositing the plug 14 in the cavity 13. More specifically, the body includes a relatively straight lower portion 20a and an upper curved portion 20b. The end of the upper curved portion is provided with a flat area 28 so that it may be tapped with a mallet 29 such as shown in FIG. 3, for facilitating locating the device at the desired depth in the cavity. Transversely opposed aperatures 30 (only one shown) are provided closely adjacent the flat area 28 for facilitating removal of the device from the cavity once the plug 14 has been deposited therein. Further, the relatively straight portion 20a is provided with a longitudinally extending scale 31, preferably metric, for accurately determining the depth to which the device is to be inserted into the cavity.

The pusher 21, which is telescopically received within the straight portion 20a of the hollow body member 20 includes a cylindrical plate 32 which is adapted to move through the die 19 (see FIG. 5). To this end, the plate 32 is attached to an upstanding rod 33 which extends through an opening 34 provided in the body member 20 so that it may be grasped and moved axially to and fro to move the plate 32 through the die 19.

In using the device 18, the die 19 is unscrewed from the body member 20 and, as illustrated in FIG. 3, set on the femoral head 35 which has been cut in a conventional manner from the femur shaft 12 and is to be discarded. The plug 14 is then formed within the cutting portion 22 of the die by tapping a protecting plate 36 set on the attaching portion 23 with sufficient force so as to drive the cutting portion into the bone of the head 35, thus forming and retaining the plug 14 within the die 19.

Referring now to FIG. 4, the die 19 is reattached to the body member 20 with the pusher 21 in place and the device is inserted into the cavity 13 at the desired depth by use of the scale 31. As shown in dashed lines in FIG. 5, the plug is pushed from the die 19 by the pusher 21 to be deposited at an exact position over the opening into the intramedullary canal 15. Of course, the diameter of the plug is of sufficient size to close the opening into the canal.

Next, the cement 16, in the liquid state, is injected into the cavity 13 under pressure by a gun (not shown) which forces the cement to flow into the small interstices 17 of the bony structure forming the cavity. After the cavity is filled with cement, the prosthesis 11 is pushed with a steady force into the cement-filled cavity and when the cement cures is firmly bonded to the femur shaft 12. Accordingly, a superior cement interface is formed in the bony structure of the cavity and a superior fixation of the prosthesis is obtained.

It is to be understood that the form of the invention herewith shown and described is to be taken as an illustrative embodiment only of the same and that various changes in the shape, size and arrangement of the parts may be resorted to without departing from the spirit of the invention.

We claim:

1. A method of implanting a femoral prosthesis in a femur shaft, comprising the steps of:
   a. Forming a cavity opening into the intramedullary canal of the femur shaft;
   b. Depositing a plug at an exact predetermined depth between the cavity and the opening into the canal with a plug inserter into the canal;
   c. Forming the plug in a die and employing the die to position the plug in an exact predetermined position between the cavity and the opening into the intramedullary canal; and
   d. Filling the cavity with a cement in the liquid state under pressure whereby the liquid cement is forced into the small interstices of the bony structure forming the cavity without flowing into the distal portions of the canal.

2. A method of implanting a femoral prosthesis in a femur shaft as claimed in claim 1 wherein the plug is formed from a bone material.

3. A device for positioning a plug at an exact depth in a cavity formed in a femur shaft opening into the intramedullary canal, comprising:
   a. A die for cutting and retaining the plug;
   b. An elongated hollow body having an open end for detachably connecting the die thereto;
   c. A scale defined on said body for determining the depth at which the plug may be released from said device;
   d. Means for detachably connecting said die to said hollow body; and
   e. Means for releasing the plug from said die.

4. A device for positioning a plug at an exact depth in a femur shaft as claimed in claim 3 wherein said scale is a metric scale.

5. A device for positioning a plug at an exact depth in a cavity formed in a femur shaft opening into the intramedullary canal, comprising:
   a. A die for cutting and retaining the plug;
   b. An elongated hollow body having an open end for detachably connecting the die thereto;
   c. Means for detachably connecting said die to said hollow body;
   d. Means for releasing the plug from said die; and
   e. Said means for releasing said plug from said die comprises a pusher element telescopically mounted within said body for movement to and fro relative thereto; and said pusher comprises a cylindrical plate and an attached upstanding rod extending outside of said body.

* * * * *